United States Patent [19]

Kaiser et al.

[11] Patent Number: 4,529,604
[45] Date of Patent: Jul. 16, 1985

[54] N,N-DI-(N-PROPYL)DOPAMINE DERIVATIVES

[75] Inventors: Carl Kaiser, Haddon Heights, N.J.; Alfonso J. Tobia, Bucks County, Pa.

[73] Assignee: SmithKline Beckman Corporation, Philadelphia, Pa.

[21] Appl. No.: 782,198

[22] Filed: Mar. 28, 1977

[51] Int. Cl.$^3$ .................... C07C 91/32; A61K 31/138
[52] U.S. Cl. ................................ 514/654; 564/374; 514/929
[58] Field of Search ............... 260/479 R, 570.8 R; 424/311, 330; 564/374

[56] References Cited

U.S. PATENT DOCUMENTS 3,686,167  8/1972  Fujimura et al. ............... 260/479 R
4,219,568  8/1980  Goldberg et al. ................ 424/330

OTHER PUBLICATIONS

Volkman et al., Federation Proceedings, V.36, No. 3, Mar. 1, 1977, AB No. 4093, p. 1049.

Kindler et al., CA 45, 1970–1971 (1951).
Genos et al., J. Med. Chem. 18, 1194–1200 (1975).
Cannon et al., J. Med. Chem. 18, 1212–1216 (1975).

*Primary Examiner*—Robert Gerstl
*Attorney, Agent, or Firm*—Richard D. Foggio; Alan D. Lourie

[57] ABSTRACT

N,N-Di-(n-propyl)dopamine derivatives having peripheral dopamine receptor agonist activity prepared by synthetic routes known for phenethylamines. The renal vasodilator effect of 3,4-dihydroxy-N,N-di(n-propyl)-phenethylamine is potentiated by the concomitant administration of the β-blocker propranolol.

3 Claims, No Drawings

N,N-DI-(N-PROPYL)DOPAMINE DERIVATIVES

This invention relates to novel N,N-di(n-propyl)-dopamine derivatives which are stimulants of peripheral dopamine receptors. More specifically, the dopamine derivatives of this invention increase renal blood flow. Of particular importance is the selective renal vasodilator activity produced by these compounds as outlined more fully below. Stimulants of peripheral dopamine receptors are therefore especially useful as antihypertensive agents.

The dopamine derivatives of this invention are represented by the following structural formula:

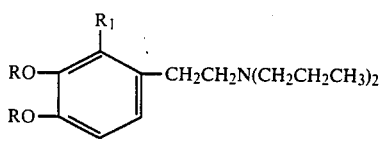

FORMULA I in which:

R is hydrogen or acetyl; and $R_1$ is hydrogen, halogen such as chloro, bromo, or fluoro, or lower alkyl of from 1 to 3 carbon atoms.

Particular compounds of this invention represented by formula I above are 3,4-dihydroxy-N,N-di(n-propyl)phenethylamine; 3,4-diacetoxy-N,N-di-(n-propyl)phenethylamine; 2-chloro-3,4-dihydroxy-N,N-di-(n-propyl)phenethylamine; and 3,4-dihydroxy-2-methyl-N,N-di(n-propyl)phenethylamine.

The pharmaceutically acceptable acid addition salts having the utility of the free bases of formula I, prepared by methods well known to the art, are formed with both inorganic or organic acids, for example: maleic, fumaric, benzoic, ascorbic, pamoic, succinic, bis-methylenesalicylic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

The compounds of formula I are prepared from various synthetic routes known for phenethylamine derivatives. For example, starting with a 3,4-dimethoxy-phenylacetic acid derivative, treatment with thionyl chloride gives the acid chloride which is treated with N,N-di-(n-propyl)amine and the resulting acetamide is reduced by means of, for example, boron hydride or lithium aluminum hydride in a solvent such as tetrahydrofuran. Demethylation with either 48% hydrobromic acid or boron tribromide furnishes the 3,4-dihydroxy product.

Alternatively, a 3,4-dimethoxyphenethylamine derivative is treated with propionic anhydride or propionyl chloride to give the propionamide which is either reduced with boron hydride and then reacted with propionic anhydride or treated with n-propyl bromide and the resulting N-(n-propyl)propionamide is reduced with boron hydride or lithium aluminum hydride. Demethylation with 48% hydrobromic acid or boron tribromide again yields the 3,4-dihydroxy product.

The 3,4-diacetoxy products of formula I are prepared from the corresponding 3,4-dihydroxy derivative by acylation with acetic anhydride or acetyl chloride.

As stated above, the compounds of this invention stimulate peripheral dopamine receptors, for example they increase renal blood flow and have as an end utility hypotensive activity. The renal vasodilator activity of the compounds of formula I is measured in an anesthetized dog. In this pharmacological procedure, a test compound is administered at progressively increasing (3-fold) infusion rates of 0.1 to 810 mcg/kg/min or 3 to 300 mcg/kg/min for 5 minutes each to anesthetized normotensive dogs and the following parameters are measured: renal artery blood flow, iliac artery blood flow, arterial blood pressure and heart rate. Results are reported as a percent change, increase or decrease, at time of peak response (from pre-drug controls) and for a significant effect renal blood flow (increase) and renal vascular resistance (decrease) should be approximately 10% or greater. The effect on renal vascular resistance can be calculated from any change in renal blood flow and arterial blood pressure.

An advantageous compound of formula I, 3,4-dihydroxy-N,N-di-(n-propyl)phenethylamine, upon administration by i.v. infusion in the dog as described above decreased arterial blood pressure and renal vascular resistance while renal blood flow increased. Heart rate was virtually unchanged. The $ED_{15}$ (cumulative dose by infusion which produces a 15% decrease in renal vascular resistance) is 100 mcg/kg with a maximum decrease of 34%. Blockade of this renal vasodilator response by the dopamine receptor antagonist bulbocapnine indicates a dopaminergic mechanism of action. 3,4-Diacetoxy-N,N-di-(n-propyl)phenethylamine produced significant renal vasodilator effects at doses of 30 and 300 mcg/kg/min. Another compound, 2-chloro-3,4-dihydroxy-N,N-di-(n-propyl)phenethylamine, showed a similar cardiovascular profile as its 2-des-chloro congener although somewhat less potent.

The pharmaceutical compositions of this invention having peripheral dopaminergic activity are prepared in conventional dosage unit forms by incorporating a compound of formula I or a pharmaceutically acceptable acid addition salt thereof, in a nontoxic amount sufficient to stimulate peripheral dopamine receptors in an animal, with a nontoxic pharmaceutical carrier according to accepted procedures. Preferably the compositions will contain the active ingredient in an active but nontoxic amount selected from about 10 mg. to about 1000 mg. of active ingredient per dosage unit.

The pharmaceutical carrier employed may be, for example, either a solid or liquid depending on whether the final formulation will be administered orally or parenterally. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent may include any time delay material well known to the art, such as glyceryl, monostearate or glyceryl distearate alone or with a wax.

A wide variety of pharmaceutical forms can be employed to accomodate oral or parenteral administration. Thus, if a solid carrier is used the preparation can be tableted, placed in a hard gelatin capsule in powder or pellet form, or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul or for i.v. infusion, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to the desired end product.

The method of stimulating peripheral dopamine receptors in accordance with this invention comprises administering internally to an animal requiring stimulation of said peripheral dopamine receptors a compound of formula I or a pharmaceutically acceptable acid addition salt thereof, usually combined with a pharmaceutical carrier, in a nontoxic amount sufficient to stimulate said peripheral dopamine receptors. The active ingredient will be administered preferably in a dosage unit, in an active, nontoxic quantity selected from about 10 mg. to about 1000 mg. of the parent chemical of formula I. The route of administration may be orally or parenterally. Advantageously equal doses will be administered three times a day with the daily dosage regimen being selected from about 30 mg. to about 3000 mg. For administration by i.v. infusion, for example over a ten to thirty minute period, a total dose selected from about 0.1 mg. to about 50 mg. will be administered. When the method described above is carried out, stimulation of peripheral dopamine receptors is produced resulting in a renal vasodilator/hypotensive effect with a minimum of side effects.

A striking feature of this invention is the marked potentiation by the β-adrenergic blocker propranolol of the renal vasodilator effects of 3,4-dihydroxy-N,N-di-(n-propyl)phenethylamine. In the presence of propranolol the $ED_{15}$ for decrease in renal vascular resistance is reduced from 100 mcg/kg to 3 mcg/kg. This effect of propranolol pretreatment on 3,4-dihydroxy-N,N-di-(n-propyl)phenethylamine is summarized in the following table:

| GROUP (3 Dogs) | Average Maximal % Change (mean values ± standard errors) | | | | | | | | $ED_{15}$ mcg/kg |
|---|---|---|---|---|---|---|---|---|---|
| | RBF | | RVR | | MABP | | HR | | |
| Compound[a] | +30 | ±13 | −34 | ±6 | −16 | ±3 | −10 | ±2 | 100.0 |
| Compound + Propranolol[b] | +136 | ±44 | −64 | ±7 | −23 | ±2 | −9 | ±3 | 3.4 |

RBF = renal blood flow; RVR = renal vascular resistance;
MABP = mean arterial blood pressure; HR = heart rate
[a]3,4-Dihydroxy-N,N—di-(n-propyl)phenethylamine infused at progressively increasing (3-fold) doses beginning at 0.1 mcg/kg/min up to 810, each dose infused for 5 minutes
[b]Propranolol pretreatment given intravenously, 2 mg/kg Included within this invention are combination compositions having peripheral dopaminergic activity comprising per dosage unit 3,4-dihydroxy-N,N-di-(n-propyl)phenethylamine or a pharmaceutically acceptable acid addition salt thereof in an active but nontoxic amount selected from about 10 mg. to about 1000 mg. and from about 1 mg. to about 480 mg. of propranolol. This combination is useful as a renal vasodilator/hypotensive composition.

A further feature of this invention is the method of stimulating peripheral dopamine receptors which comprises administering internally to an animal requiring stimulation of said peripheral dopamine receptors a nontoxic amount of 3,4-dihydroxy-N,N-di-(n-propyl)phenethylamine or a pharmaceutically acceptable acid addition salt thereof, concomitant with a nontoxic potentiating amount of propranolol. The active ingredients are preferably combined with a pharmaceutical carrier and administered by a route which effectively transports the active agents to the dopamine receptors which are to be stimulated such as orally or parenterally. In carrying out this method the amount of said phenethylamine ingredient is selected from about 0.1 to 50 mg/kg and the amount of propranolol is selected from about 0.01 to 8 mg/kg. The combination composition will be administered usually 1 to 4 times daily.

The following examples illustrate the preparation of specific compounds falling within the scope of formula I and their formulation in pharmaceutical compositions of this invention and as such are not to be construed as limitations.

EXAMPLE 1

To a solution of 20 g. (0.10 mole) of 3,4-dimethoxyphenylacetic acid in 100 ml. of benzene was added dropwise 70 ml. (115 g., 0.98 mole) of thionyl chloride. The solution was heated to 50° C. for two hours, then evaporated in vacuo to give a residue of 3,4-dimethoxyphenylacetyl chloride. A solution of 21.4 g. (0.10 mole) of the acid chloride in 70 ml. of chloroform was added with stirring to a solution of 70 ml. of chloroform and 22.2 ml. (30.0 g., 0.30 mole) of N,N-di-(n-propyl)amine at 0° C. The resulting mixture was heated at 50° C. for two hours, cooled, diluted and washed with dilute hydrochloric acid, dilute sodium carbonate solution and water. The dried chloroform solution was evaporated in vacuo to give N,N-di(n-propyl)-3,4-dimethoxyphenylacetamide.

To 200 ml. (0.20 mole) of a 1M solution of diborane in tetrahydrofuran cooled in an ice bath was added dropwise a solution of 27.8 g. (0.10 mole) of N,N-di-(n-propyl)-3,4-dimethoxyphenylacetamide in about 200 ml. of anhydrous tetrahydrofuran, under argon. The mixture was refluxed for one and one-quarter hours, cooled and methanol added carefully. When the bubbling subsided the reaction mixture was evaporated in vacuo. The residue was dissolved in methanol, ethereal hydrogen chloride was added and the mixture evaporated in vacuo slowly. This residue was dissolved in water, washed with ether, basified and extracted with ether. The dried solution was evaporated to yield N,N-di-(n-propyl)-3,4-dimethoxyphenethylamine.

A solution (150 ml.) of boron tribromide/methylene chloride (1 g./5 ml., 0.12 mole) was added to a solution of 5.0 g. (0.019 mole) of N,N-di-(n-propyl)-3,4-dimethoxyphenethylamine in 100 ml. of methylene chloride, cooled in an ice bath. The bath was removed and the reaction mixture was stirred at room temperature. Methanol (about 50 ml.) was added to the reaction mixture, with cooling, and the resulting solution was evaporated in vacuo. The residue crystallized to give 3,4-dihydroxy-N,N-di-(n-propyl)phenethylamine hydrobromide, m.p. 153.5°–154.5° C.

EXAMPLE 2

A mixture of 3.0 g. (0.0094 mole) of 3,4-dihydroxy-N,N-(n-propyl)phenethylamine hydrobromide in 100 ml. of acetic anhydride was heated with stirring on the steam bath. The reaction mixture was evaporated to dryness with toluene to yield 3,4-diacetoxy-N,N-di-(n-propyl)phenethylamine hydrobromide, m.p. 119.5°–120.5° C.

EXAMPLE 3

A mixture of 10.4 g. (0.0483 mole) of 2-chloro-3,4-dimethoxyphenethylamine and 20 ml. (20.2 g., 0.155 mole) of propionic anhydride was heated on the steam bath for two hours with stirring. The reaction mixture was poured into dilute sodium hydroxide solution, stirred at room temperature and extracted with ether. The ether extract was washed with dilute hydrochloric acid and water, dried and evaporated to give N-(2-chloro-3,4-dimethoxyphenethyl)propionamide.

To 100 ml. of a solution of diborane in tetrahydrofuran (0.93 molar, 0.093 mole) was added a solution of 9.0 g. (0.033 mole) of the above-prepared propionamide. The mixture was refluxed overnight, cooled and methanol added to destroy unreacted diborane. Ethereal hydrogen chloride and methanol were added and the mixture evaporated to dryness. The residue was dissolved in dilute hydrochloric acid/ether and the acidic aqueous solution was basified, extracted with ether and the dried ether extract evaporated to yield N-(n-propyl)-2-chloro-3,4-dimethoxyphenethylamine. The latter (3.5 g., 0.0137 mole) was dissolved in 100 ml. of propionic anhydride and stirred overnight. The mixture was evaporated nearly to dryness, toluene was added and then further evaporated to leave N-(2-chloro-3,4-dimethoxyphenethyl)-N-(n-propyl)propionamide.

This propionamide in tetrahydrofuran solution was added dropwise to 75 ml. of 0.93M diborane in tetrahydrofuran (0.070 mole) at 0°–5° C. The mixture was refluxed for two and one-half hours and allowed to stand overnight. Methanol was added and the reaction mixture evaporated. Dilute hydrochloric acid was added, the mixture refluxed for two hours, cooled and washed with ether. The resulting solution was basified, extracted with ether, dried and evaporated to give 2-chloro-3,4-dimethoxy-N,N-di-(n-propyl)phenethylamine.

The phenethylamine thus prepared (3.9 g., 0.013 mole) was dissolved in 200 ml. of 48% hydrobromic acid and the mixture was heated at reflux for two hours. The reaction mixture was evaporated to dryness (with toluene), the residue was dissolved in methanol, ether was added and the solution allowed to stand overnight. Addition of ether furnished 2-chloro-3,4-dihydroxy-N,N-di-(n-propyl)phenethylamine hydrobromide, m.p. 151.5°–152.5° C.

EXAMPLE 4

Following the procedures of Example 1, 3,4-dimethoxy-2-methylphenylacetic acid is converted to its acid chloride and then reacted with N,N-di-(n-propyl)amine to give the corresponding acetamide derivative. Reduction with diborane in tetrahydrofuran followed by demethylation of the ether groups with boron tribromide yields 3,4-dihydroxy-2-methyl-N,N-di-(n-propyl)phenethylamine.

EXAMPLE 5

Employing the synthetic scheme outlined in Example 3, reaction of 2-bromo-3,4-dimethoxyphenethylamine with propionic anhydride similarly gives N-(3,4-dimethoxy-2-methylphenethyl)propionamide which is reduced with diborane to N-(n-propyl)-3,4-dimethoxy-2-methylphenethylamine. Reaction of the amine with propionic anhydride and subsequent reduction with diborane furnishes the N,N-di-(n-propyl)amine which is demethylated by treatment with 48% hydrobromic acid to give 3,4-dihydroxy-2-methyl-N,N-di-(n-propyl)phenethylamine.

EXAMPLE 6

| Ingredients | W/V percentages |
|---|---|
| 3,4-Dihydroxy-N,N—di-(n-propyl)phenethylamine (as a water soluble acid addition salt) | Equivalent to 20 mg. of free base per ml. |
| Sodium tartrate | 1 |
| Tartaric acid | 0.7 |
| Water for parenterals, q.s. | 100 |

The above ingredients are dissolved in an amount of the water equal to approximately 95% of the final volume, mixed, heated as required, cooled to room temperature and the remainder of the water is added. The solution is filtered and filled in ampuls.

Similarly addition of the equivalent of 1 mg. of propranolol (as the hydrochloride salt) to the above formulation gives a combination product in accordance with this invention.

The solutions prepared as in Example 6 are administered internally to an animal requiring stimulation of peripheral dopamine receptors (renal vasodilator/hypotensive effects) within the dose ranges set forth hereinabove.

What is claimed is:

1. A chemical compound of the structural formula:

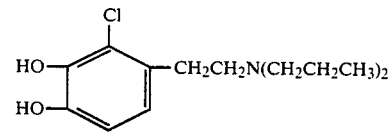

or a nontoxic pharmaceutically acceptable acid addition salt thereof.

2. A pharmaceutical composition having peripheral dopaminergic activity comprising a nontoxic, effective amount of a compound of claim 1 combined with a pharmaceutical carrier.

3. A method of producing renal vasodilator activity which comprises administering internally to an animal requiring said activity a nontoxic amount sufficient to produce said activity of a compound of claim 1.

* * * * *